United States Patent [19]

Gracovetsky

[11] Patent Number: 4,699,156
[45] Date of Patent: Oct. 13, 1987

[54] NON INVASIVE METHOD AND EQUIPMENT FOR THE DETECTION OF TORSIONAL INJURIES IN THE LUMAR SPINE OF A PATIENT

[75] Inventor: Serge Gracovetsky, St. Lambert, Canada

[73] Assignee: Diagnospine Research Inc., Montreal, Canada

[21] Appl. No.: 742,042

[22] Filed: Jun. 6, 1985

[51] Int. Cl.⁴ .............................................. A61B 5/10
[52] U.S. Cl. .................................... 128/781; 128/782
[58] Field of Search ...................... 128/774, 781.2, 653, 128/660; 33/511–512

[56] References Cited

U.S. PATENT DOCUMENTS

| | | | |
|---|---|---|---|
| 3,608,541 | 9/1971 | Hall | 128/781 |
| 4,108,164 | 8/1978 | Hall | 128/781 |
| 4,202,355 | 5/1980 | Loeffler | 128/774 |
| 4,373,532 | 2/1983 | Hill et al. | 128/660 |
| 4,506,676 | 3/1985 | Duska | 128/653 |
| 4,600,012 | 7/1986 | Kohayakawa et al. | 128/781 X |

FOREIGN PATENT DOCUMENTS

| | | | |
|---|---|---|---|
| 0140681 | 5/1985 | European Pat. Off. | 128/774 |
| 1564781 | 4/1969 | France | 128/774 |
| 2449433 | 10/1980 | France | 128/781 |
| 2491323 | 4/1982 | France | 128/774 |
| 8101506 | 6/1981 | PCT Int'l Appl. | 128/782 |
| 0646982 | 2/1979 | U.S.S.R. | 128/781 |
| 0772529 | 10/1980 | U.S.S.R. | 128/781 |
| 0933077 | 6/1982 | U.S.S.R. | 128/774 |

OTHER PUBLICATIONS

Anderson et al.; "Combined Flexi-Rule/Hydrogoniometer for Measurement of Lumbar Spine and its Sagittal Movement"; *Rheum. and Rehab.*, vol. 14, No. 3, 1975, pp. 173–179.
Terekhov; "Measuring Man's Stability of Stance"; *J. of Clin. Engr.*, vol. 4, No. 1, 1–3/1979, pp. 61–65.
Aekinson et al.; "Closed Circuit TV Movement Detector"; *Med. and Biol. Eng. and Comput.*, vol. 19, No. 6, 11-1981, pp. 789–791.

Primary Examiner—Kyle L. Howell
Assistant Examiner—Angela D. Sykes

[57] ABSTRACT

A non invasive method and equipment for the detection of a mechanical abnormality or injury, especially a torsional injury, in the lumbar spine of a patient. In a first step, any variation in the lumbar curve of the patient is measured using a non invasive technique, while the patient is performing a physical test. In a second step, any discrepancy or assymmetry away from the average response of a group of normal healthy persons is detected in the previously measured variation in the lumbar curve. In practice, the absence of any variation or the detection of a discrepancy or assymmetry in the so measured variation when compared with the average, is indicative of the presence of a mechanical abnormality or injury in the lumbar spine of the patient.

6 Claims, 5 Drawing Figures

NON INVASIVE METHOD AND EQUIPMENT FOR THE DETECTION OF TORSIONAL INJURIES IN THE LUMAR SPINE OF A PATIENT

BACKGROUND OF THE INVENTION

1. Field of the Invention

The present invention broadly relates to a non invasive method for the detection of a mechanical abnormality or injury of the lumbar spine of a patient The invention more particularly relates to a non invasive method and equipment for the detection of torsional injuries in the lumbar spine of a patient.

2. Brief Description of the State of the Art

It is well known in the medical art that common back disorders have a mechanical etiology. Pathology clearly shows that there are two common patterns of disk injuries which correspond to two different types of mechanical failure of the spine.

The first injury which is generally identified as "compression injury", starts centrally with a fracture to an end plate of a lumbar vertebra, sometimes followed by injection of part of the vertebra nucleus into the vertebral body. In this particular case of injury, neither the annulus of the disk nor the facets of the vertebra are damaged However, the injured end plate permits the invasion of the avascular nucleus and the avascular inner portion of the annulus by granulation (healing) tissue. The effect of this is to dissolve or hydrolyze the avascular portion of the disk. With progression, the disk losses its thickness while the outer layers of the annulus remain relatively well preserved. With loss of disk thickness, the facet joints of the vertebra subluxates and becomes arthritic.

In practice, the fracture on the end plate of a vertebra is an undisplaced fracture of cancelleous bone which heals rapidly. The symptoms are short lived, typically lasting two weeks. The facet joint arthritis appears late. At this stage, symptoms may also arise from a reduction in size of the spinal canal (lateral or central spinal stenosis).

The second common back disorder which is generally identified as "torsional injury", amounts to a damage of the disk annulus, which damage occurs simultaneously with a damage to the facet joints of the vertebra. The outer rings of the annulus are torn off the vertebral end plate, and separation occurs between the laminations of the annulus. There is no damage to the nucleus or to the end plate of the vertebra. The facet joints show subchondral fracture, with consequence collapse of the articular surfaces and chronic synovitis.

In this particular case, the basic injury is to collageneous ligamentous tissue which requires six weeks to regain 60% of its strength. Because the injury involves both the disk and the facet joints, it is more difficult for the joint to stabilize itself and recurrence is frequent. The condition is progressive and may lead to spinal stenosis, instability and degenerative spondilolisthesis.

In this regard, it has been shown in laboratory that a compression injury is easily produced by compressing an intervertebral joint between 2Mpa to 6Mpa. It has also been shown that a torsional injury can be seen with as little as 2 to 3 degrees of forced rotation requiring only 22 to 33 Newton meter of torque.

In practice, it has been shown that 64% of the patients complaining of backache and sciatica, or of sciatica alone, exhibit torsional injuries whereas 35% of said patients exhibit axial compression injury. The torsional injury occurs mainly at the fourth level, that is between lumbar vertebral L4 and L5. It has also been shown that almost 100% of the fourth joints problems are torsional injuries. On the other hand, almost 100% of the compression injuries occur at the L5/S1 level, that is between the 5th lumbar vertebra L5 and the 1st sacral vertebra S1. Double injuries, that is joint injured with both compression and torsion, occurs in 20% of the cases, most invariably at the L5/S1 level.

The probalities of injuries by either compression or torsion are given hereinafter in table 1. As can be seen, the importance of frequency of torsional injury cannot be overlooked. As can also be seen, the probability of a third type of injury giving symptoms is very remote. As a matter of fact, a third part of injury as so far not be recognized in autopsy material.

TABLE 1

| CLINICAL DETERMINATION OF THE VARIOUS PROBABILITIES OF INJURIES | | | |
|---|---|---|---|
| JOINT | P (injury) | P (compression) | P (torsion) |
| L5/S1 | 47% | 98% | 22% |
| L4/L5 | 47% | 1%< | 76% |
| L3/L4 | 5%< | 1%< | 1%< |
| L2/L3 | 1%< | 1%< | 1%< |
| L1/L2 | 1%< | 1%< | 1%< |
|  | 100% | 100% | 100% |

It should be noted from the above description of pathology that both types of injuries can give rise to identical symptomoloty that is back pain, back pain and sciatica or sciatica alone. As a result, symptoms cannot be used to diagnose a type of injury because identical symptoms may arise from different injuries.

It is also well known in the art that low back pain is the leading cause of disability in North America today, affecting from 8 to 9 million people. It is the most common disability in persons under the age of 45 and the third after arthritis and heart decease in those over 45. It is also estimated that 2 of 3 persons would have lumbar pain at sometimes of their life, usually between the ages of 20 to 50. The fact that problems are so common in people of working age is not coincidental. Indeed, most back problems are work-related.

As the injury caused by a certain task cannot be identified from the patient's symptoms, it is not possible to relate directly a given task to an injury mode, although such a relationship is central to the definition of a task that will not injure a specific worker.

The economic effects of back pain and injury are staggering. Back problems are second only to the common cold as a cause of absenteeism in the industry. It is moreover responsible for 93 million lost workdays every year and is a leading cause of reduced work capacity.

Hence, the incentive for prevention of back injury is very large.

SUMMARY OF THE INVENTION

An object of the present invention is to provide a non invasive method for the detection of a mechanical abnormality or injury in the lumbar spine of a patient. By "non invasive" method, there is meant a method where no invasive tools such as X-rays, needles and the like are used for collecting the physiological data necessary for detecting the presence of a mechanical abnormality or injury.

Another object of the invention is to provide a non invasive method especially designed for the detection of torsional injuries in the lumbar spine of a patient.

A further object of the invention is to provide an equipment to carry out the above mentioned method.

The non invasive method according to the invention for the detection of a mechanical abnormality or injury the lumbar spine of the patient derives from an observation made by the inventor that a healthy spine is characterized by its ability to flex smoothly in any plane. Hence, an injury to any joint of the spine will always result in a reduced flexing range of motion of the spine.

Based on this particular observation, the non-invasive method according to the invention for the detection of a mechanical abnormality or injury in the lumbar spine of a patient, comprises the steps of:

measuring any variation of the lumbar curve of the patient while the same is performing a simple physical test such as walking or leaning to the right or to the left, using a non-invasive technique; and detecting any discrepancy or assymmetry away from the average response of a group of normal healthy persons in said measured variation of lumbar curve.

In this particular method, the absence of any variation in the lumbar curve or the detection of any discrepancy or assymmetry in the measured variation when compared with the average, will be indicative of the presence of a mechanical abnormality or injury in the lumbar spine of the patient.

This non invasive method is particularly useful for the detection of torsional injuries in the lumbar spine of the patient. In this particular case, the method may comprise the steps of:

(a) detachably fixing a string of skin-markers onto the skin of the back of the patient in the midline of his spine from at least thoracic vertebra T10 down to at least sacral vertebra S3;

(b) monitoring and recording with a visualization equipment, the relative positions of the skin-markers on the back of the patient as he leans to the left and then to the right off his saggital plane;

(c) comparing the recorded positions of the skin markers when the patient was leant to the left, with the recorded positions of said skin-markers when the patient was leant to the right in order to determine whether there is a significant difference between both of said recorded positions; and (d) in the case where there is such a significant difference, determining whether the different recorded positions are symmetrical with respect to the saggital plane of the patient.

In this particular case, the observation of a non significant difference between the recorded positions of the skin-markers indicate a refusal by the patient to flex his spine, such a refusal in turn indicating the presence of a double torsional injury having damaged a lumbar intervertebral joint statistically between vertebral L4 and L5 or L5 and S1. On the other hand, provided that the recorded positions of the skin-markers are different, the observation of a substantial assymmetry the recorded positions will indicate the refusal by the patient to flex his spine in one direction, such a refusal in turn indicating the presence of a simple torsional injury at any lumbar inter vertebral joint statiscally between vertebrae L4 or L5 or L5 and S1.

As visualisation equipment, use can be made of a high resolution T.V. camera or of a pair of high resolution T.V. cameras spaced apart from each other in order to monitor and record the relative positions of the skin-markers in the space and thus determine any variation of lumbar curve in every spatial direction when the patient is leaning to the right and to the left. In this particular case, the skin-markers must of course be of the visible type.

Alternatively, use can be made of an ultrasonic or laser equipment to visualize the relative positions of the markers in the space. When use is made of such an ultrasonic technique, the equipment may comprise a plurality of small ultrasonic emitters used as skin markers, and a set of three receivers.

The equipment that can be used in accordance with the present invention for the detection of personal injury in the lumbar spine of the patient, may comprise:

(a) a plurality of skin-markers attachable to the skin of the back of the patient to form a string along the midline of his spine from at least thoracic vertebra T10 down to at least sacral vertebra S3;

(b) a visualization equipment for monitoring the relative positions of said skin-markers on the back of the patient as he leans to the left and to the right off his saggital plane;

(c) means for recording the monitored positions of the skin-markers when the patient is leaning to the left and to the right; and (d) means for comparing the recorded positions of the skin-markers when the patient was leant to the left with the recorded positions of said skin-markers when the patient was leant to the right in order to determine whether there is a significant difference therebetween and, in the case where there is such a difference, whether the different recorded positions are symmetrical with respect to the saggital plane.

BRIEF DESCRIPTION OF THE DRAWINGS

The invention will be better understood with reference to the following, non restrictive description of a preferred embodiment thereof, given with reference to the accompanying drawings wherein.

DESCRIPTION OF TWO PREFERRED EMBODIMENTS OF THE INVENTION

Figure 1:
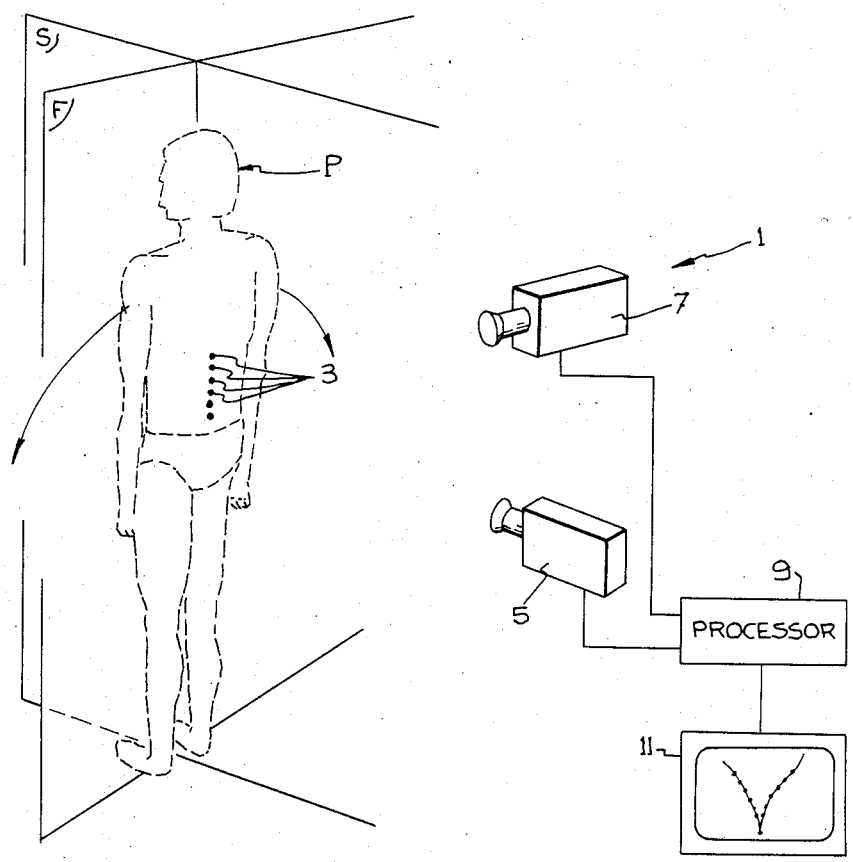
FIG. 1 is a schematic view of a non-invasive equipment for the detection of torsional injuries in the lumbar spine of a patient.

The first equipment 1 as shown in FIG. 1, is intended to be used for the detection of torsional injury in the lumbar spine of a patient P. This equipment 1 comprises a plurality of skin-markers 3 attachable to the skin of the back of the patient P to form a string along the midline of his spine from at least thoracic vertebra T10 down to at least sacral vertebral S3. The skin-markers 3 may consist of dots of contrasting colours stickable to the skin of the patient. Alternatively, these markers may consist of LED's fixable to the back of the patient in order to form a luminous string along the midline of his spine.

The equipment 1 also comprises a visualization equipment for monitoring the relative positions of the skin-markers on the back of the patient as the same leans to the left and to the right with respect to his saggital plane S, preferably in his frontal plane F as shown with the arrows in FIG. 1. This visualization equipment may consist of a photographic camera preferably capable of taking stop action photography. However, this visualization equipment preferably consists of at least one and preferably two high resolution TV cameras 5 and 7 positioned in such a manner as to monitor the relative positions of the skin-markers on the back of the patient as the same leans to the left and to the right of his saggital plane S. The use of two spaced apart cameras instead of one has the major advantage of monitoring the relative positions of the skin-markers in the space, instead of monitoring them in a plane.

Means 9 are provided for recording the relative positions of the skin-markers monitored by the cameras 5 and 7 when the patient is leaning to the left and to the right. These recording means 9 may include means for processing the information recorded by both cameras 5 and 7 in order to determine the spatial relationship between the various skin-markers as the patient flexes his spine.

In addition, the equipment 1 comprises means 11 for comparing the recorded positions of the skin-markers when the patient was leant to the left with the recorded position of the skin-markers 3 when the patient P was leant to the right in order to determine whether there is a significant difference then between and, in the case where there is such a difference, whether the different recorded positions are symmetrical with respect to the saggital plane S of the patient P.

Advantageously, these means 11 for comparing the recorded positions of the skin-markers 3 may consist of a TV monitor on which both recorded positions may be displayed simultaneously. Of course, the processor 9 and/or TV monitor 11 may comprise means for storing on line the recorded positions and for recalling them whenever necessary.

Figure 2:
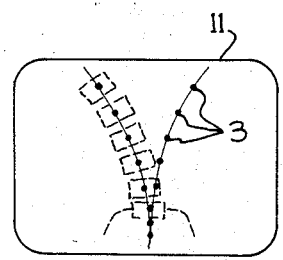
FIG. 2 is a schematic representation of the data recorded with the equipment of FIG. 1 in the case of a normal healthy person.

FIG. 2 is a diagrammatic representation of the recorded strings or the TV monitor 11 in the case of a normal healthy patient capable of freely flexing his spine. In this FIG. 2, the pelvis and lumbar vertebrae of the patient have been shown in dotted lines, for the purpose of clarification.

The important, right and left bents and the symmetry of the recorded position as shown in FIG. 2 is a clear indication that a patient is normal and does not suffer any torsional injury.

In this regard, it may be noted that, in order to bend sideways, the spine must have a certain amount of lordosis. When there exist lordosis and the patient is bending laterally, an axial torque is induced. The fact that there is symmetry in the right and left motion indicates the torque created at all joints does not disturb the patient. Hence, we may conclude that there is no evidence of torsional injury.

Figure 3:
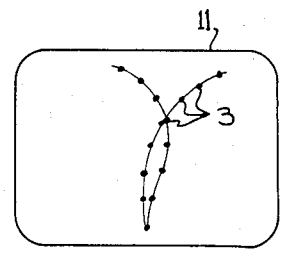
FIG. 3 is a schematic representation of the data recorded with the equipment of FIG. 1 in the case of a patient with a simple torsional injury.

FIG. 3 is a schematic representation of the recorded positions of the skin-markers 3 in the case of a patient suffering a simple torsional injury. As can be seen, the recorded positions shows a strong dissymmetry.

In this particular case, it is clear that the spinous process of joint L3/L4 is shifted to the left, which means a torsional injury at intervertebral joint L4-L5. This in turn means that the patient has probably damaged in his facets in such a way that the right facet is injured by excessive compression. This injury could occur when the patient pulls an object with his right arm. In this case, the pelvis is driving the spine, forcing all right facets to be subjected to compression.

As aforesaid, to bend sideways, the spine needs lordosis. A patient with torsional injury immediately reduces his lordosis.

When required to bend to the right, the patient must allow some lordosis. Therefore, there must be an axial reduced torque that will rotate pelvis counterclockwisely. In this particular position, the right facet will be under compression and the spine will be driving the pelvis. Of course, this lateral bend will increase the injury unless compensated. To do so, the patient must first of all prevent the lateral bend to the right. Hence, to protect his intervertebral joints L4/L5 which has been injured the spine will bend to the left. By doing so, the induced clockwise axial torque will protect the damaged L4/L5 joint. Then, the remainder of the spine will attend to bend on the right, as requested. Provided that the torsional injury was only to the L4/L5 level with the right facet damaged by excessive compression, there will be no objection for the patient to fully bend to the left. However, a torsional injury will always damage both facets, the left facet being damaged because some of the capsular ligaments have been overstretched. Hence, with repeated injury, the left facet may not be able to take a full and normal compression. As a result, the patient in this particular case will bend on the left but not too much because he does not fully release his lordosis.

This particular pathology is the one illustrated in FIG. 3.

Figure 4:
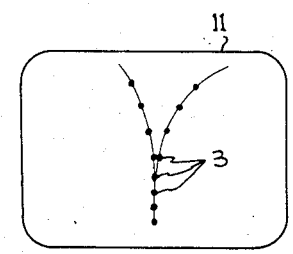
FIG. 4 is a schematic representation of the data recorded with the equipment of FIG. 1 in the case of a patient with a double torsional injury.

FIG. 4 is a schematic representation of the recorded skin-markers in the particular case of a patient with a double torsional injury.

In this particular case, the patient will exhibit symmetry but much reduced lateral bent, essentially because the damages on the right and left facets are equal. This is indicative of a double torsional injury in which, at intervertebral joint L4-L5, the entire annulus was damaged due to over-rotation both clockwise by and counterclockwisely. Then, the patient will refuse to release any lordosis to prevent any axial torque to be induced.

Another explanation for that would be that if the intervertebral joint L4-L5 has lost its thickness, then the joint is unstable. In this particular case, a very little torque would be taken either clockwisely or counterclockwisely. Hence again, the patient simply could not afford to release his lordosis.

As can now be better understood, the observation of a non significant difference between the recorded positions of the skin-markers, indicates a refusal by the patient to flex his spine, such a refusal in turn indicating the presence of a double torsional injury having damaged any lumbar intervertebral joints statiscally between vertebrae L4 or L5 or L5 and S1 (see FIG. 4). However, provided at a recorded position of a skin-markers are different, the observation of the substantial assymmetry between the recorded positions indicates that the patient refuses to flex his spine in one direction, such a refusal indicating in turn the presence of a simple torsional injury at any lumbar intervertebral joint statistically vertebrae L4 and L5 or L5 and S1 (see FIG. 3).

Figure 5:
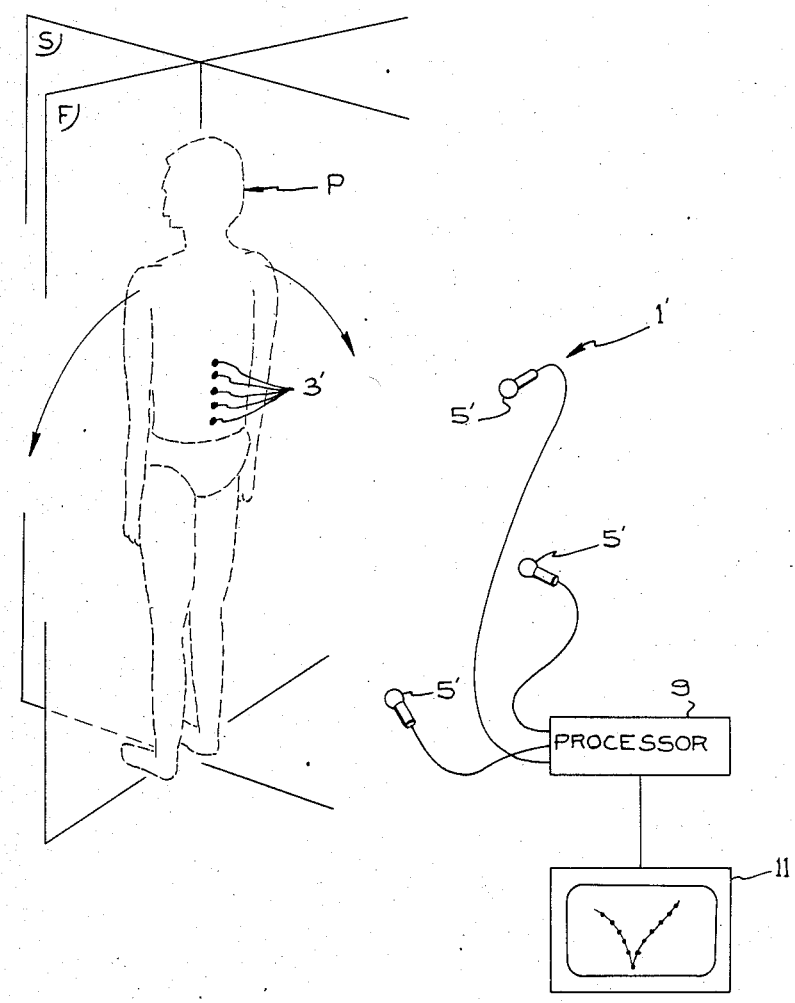
FIG. 5 is a schematic view of another, non-invasive equipment according to the invention.

The second equipment 1' as shown in FIG. 5 is substantially identical in purpose and use to the equipment 1 of FIG. 1, except that it makes use of an ultrasonic technique rather than an optical technique to measure the variation of the lumbar curve of the patient.

In this particular case, the skin-markers 3' consist of a plurality of small ultrasonic emitters fixed to the skin of the patient and adjusted to each emit at a different frequency. On the other hand, the visualization equipment comprises three spaced apart receivers 5' that may receive the signals emitted by all the emitters 3'. The received signals are supplied to a processor 9' which discriminates each signal from the others and determines the spatial position of the corresponding emitter with respect to the three receivers.

Of course, the treatment of the collected data and the interpretation of the results remain identical.

It is to be understood that other visualization techniques may also be used within the scope of the present invention to measure the variation of the lumbar curve of the patient, such as, for example, laser scanning or other optical technique.

Although the masculine pronoun has been used for consistency in style, it should be interpreted in the above specification and the following claims, to also include the feminine.

I claim:

1. A non-invasive method for the detection of torsional injuries in the lumbar spine of a patient, comprising the steps of:
    (a) detachably fixing a string of separate, dot-sized skin-markers onto the skin of the back of the patient in the middle of his spine from at least thoracic vertebra T10 down to at least sacral vertebra $S_3$;
    (b) monitoring and recording the relative positions of said skin-markers on the back of the patient as he leans to the left and then to the right off his saggital plane;
    (c) comparing the recorded positions of the skin-markers when the patient was leant to the left with the recorded positions of said skin-markers when the patient was leant to the right in order to determine whether there is a significant difference between both of said recorded positions; and
    (d) in the case where there is such a significant difference, determining whether said different recorded positions are symmetrical with respect to the saggital plane, wherein:
    the observations of a non significant difference between the recorded positions of the skin-markers indicates a refusal by the patient to flex his spine, such a refusal in turn indicating the presence of a double torsional injury having damaged any lumbar intervertebral joints statistically between vertebrae $L_4$ and $L_5$ or $L_5$ and $S_1$; and
    provided that the recorded positions of said skin-markers are different, the observation of a substantial assymmetry between said recorded positions indicates a refusal by the patient to flex his spine in one direction, such a refusal in turn indicating the presence of a simple torsional injury at any lumbar intervertebral joints statistically between vertebrae $L_4$ and $L_5$ or $L_5$ and $S_1$.

2. The method of claim 1, wherein use is made in step (a) of skin-markers of the visible type and wherein step (b) is carried out with at least one camera.

3. The method of claim 2, wherein step (b) is carried out with a pair of cameras spaced-apart from each other in order to monitor and record the relative positions of the skin-markers in the space and thus determine any variation of lumbar curve in every spatial direction when the patient is leaning to the right and to the left.

4. A kit for the detection of torsional injuries in the lumbar spine of a patient, said equipment comprising:
    (a) a plurality of separate, dot-sized skin-markers attachable to the skin of the back of the patient to form a string along the midline of his spine from at least thoracic vertebra $T_{10}$ down to at least sacral vertebra $S_3$:
    (b) a visualization equipment means for observing and monitoring the relative positions of said skin-markers on the back of the patient as he leans to the left and to the right off his saggital plane;
    (c) means connected to the visualization equipment means for recording the monitored positions of the skin-markers when the patient is leaning to the left and to the right; and
    (d) means connected to the recording means for comparing the recorded positions of the skin-markers when the patient was leant to the left with the recorded position of said skin-markers when the patient was leant to the right in order to determine whether there is a significant difference therebetween and, in the case where there is such a difference, whether the different recorded positions are symmetrical with respect to the saggital plane.

5. The kit of claim 4, wherein said skin-markers are of the visible type, said visualization equipment means comprises at least one camera and said means for comparing the recorded positions comprises a T.V. monitor on which both recorded positions may be displayed simultaneously.

6. The kit of claim 5, wherein said visualization kit comprises another camera for monitoring the relative positions of the skin-markers on the back of the patient from a spaced-apart position with respect to the one camera, and wherein means are provided for processing the information recorded by both cameras in order to termine the spatial relationship between the various skin-markers as the patient flexes his spine.

* * * * *